United States Patent
Li et al.

(10) Patent No.: US 11,969,349 B2
(45) Date of Patent: Apr. 30, 2024

(54) IMPLANTS FOR BONE AND CARTILAGE REPAIR

(71) Applicant: Collagen Matrix, Inc., Franklin Lakes, NJ (US)

(72) Inventors: Shu-Tung Li, Wyckoff, NJ (US); Hui-Chen Chen, Wayne, NJ (US); Debbie Yuen, Woodcliff Lake, NJ (US)

(73) Assignee: Collagen Matrix, Inc., Oakland, NJ (US)

( * ) Notice: Subject to any disclaimer, the term of this patent is extended or adjusted under 35 U.S.C. 154(b) by 46 days.

(21) Appl. No.: 17/199,920

(22) Filed: Mar. 12, 2021

(65) Prior Publication Data

US 2021/0196464 A1 Jul. 1, 2021

Related U.S. Application Data

(63) Continuation of application No. 15/241,568, filed on Aug. 19, 2016, now Pat. No. 10,945,846, which is a
(Continued)

(51) Int. Cl.
*A61F 2/28* (2006.01)
*A61F 2/30* (2006.01)
(Continued)

(52) U.S. Cl.
CPC ............ *A61F 2/28* (2013.01); *A61F 2/30756* (2013.01); *A61L 27/12* (2013.01); *A61L 27/24* (2013.01); *A61L 27/3847* (2013.01); *A61L 27/3852* (2013.01); *A61L 27/54* (2013.01); *A61L 27/58* (2013.01); *A61F 2002/2839* (2013.01);
(Continued)

(58) Field of Classification Search
CPC ...... A61L 27/50; A61L 27/52; A61F 2/30756; A61F 2/28; A61F 2002/2835; A61F 2002/30029; A61F 2002/2842; A61F 2002/2839
See application file for complete search history.

(56) References Cited

U.S. PATENT DOCUMENTS

| | | |
|---|---|---|
| 3,157,524 A | 11/1964 | Artandi |
| 4,795,467 A | 1/1989 | Piez et al. |
| (Continued) | | |

FOREIGN PATENT DOCUMENTS

| | | | |
|---|---|---|---|
| CA | 2750605 A1 * | 7/2010 | ............... A61F 2/02 |
| EP | 0309241 A2 | 3/1989 | |

OTHER PUBLICATIONS

Brittberg et al "Treatment of Deep Cartilage Defects in the Knee with Autologous Chondrocyte Transplantation" The New England Journal of Medicine vol. 331, pp. 889-895, 1994.
(Continued)

*Primary Examiner* — Christie Bahena
(74) *Attorney, Agent, or Firm* — Morse, Barnes-Brown & Pendleton, P.C.; Russell L. Widom

(57) ABSTRACT

An implant for the repair of bone and cartilage that includes a cell conductive zone that contains biopolymeric fibers and an osteoconductive zone that contains biopolymeric fibers and calcium-containing mineral particles. The biopolymeric fibers from one zone overlap with the fibers in the other zone forming a stable physical and mechanical integration of the two zones, thus conferring in vivo stability to the implant.

20 Claims, 1 Drawing Sheet

Related U.S. Application Data continuation of application No. 13/530,297, filed on Jun. 22, 2012, now abandoned.

(51) Int. Cl.

| *A61L 27/12* | (2006.01) |
|---|---|
| *A61L 27/24* | (2006.01) |
| *A61L 27/38* | (2006.01) |
| *A61L 27/54* | (2006.01) |
| *A61L 27/58* | (2006.01) |

(52) U.S. Cl.
CPC ........... *A61F 2002/30016* (2013.01); *A61F 2002/30062* (2013.01); *A61F 2002/30293* (2013.01); *A61F 2002/3092* (2013.01); *A61F 2310/00371* (2013.01); *A61L 2430/02* (2013.01); *A61L 2430/06* (2013.01)

(56) References Cited

U.S. PATENT DOCUMENTS

| 5,231,169 | A | 7/1993 | Constantz et al. |
|---|---|---|---|
| 5,326,350 | A | 7/1994 | Li |
| 5,455,231 | A | 10/1995 | Constantz et al. |
| 5,573,771 | A | 11/1996 | Geistlich et al. |
| 5,607,474 | A | 3/1997 | Athanasiou et al. |
| 5,776,193 | A | 7/1998 | Kwan et al. |
| 6,090,996 | A | 7/2000 | Li |
| 6,187,047 | B1 | 2/2001 | Kwan et al. |
| 6,203,573 | B1 | 3/2001 | Walter et al. |
| 6,626,950 | B2 | 9/2003 | Brown et al. |
| 6,716,225 | B2 | 4/2004 | Li et al. |
| 6,783,712 | B2 | 8/2004 | Slivka et al. |
| 7,166,133 | B2 | 1/2007 | Evans et al. |
| 7,381,224 | B1 | 6/2008 | Li et al. |
| 2004/0180091 | A1 | 9/2004 | Lin |
| 2008/0260794 | A1 | 10/2008 | Lauritzen |
| 2010/0248368 | A1 | 9/2010 | Lynn et al. |

OTHER PUBLICATIONS

Chen et al "A Collagen-Anorganic Bone Composite for Bone Repair: Part 1, In Vitro Characterization Studies" Transactions of the 31st Annual Meeting of the Society of Biomaterials vol. 29, 2006.

Ding et al "Age Variations in the Properties of Human Tibial Trabecular Bone" British Editorial Society of Bone and Joint Surgery vol. 79, 1997.

Doi "Sintered Carbonate Apatites as Bone Substitutes" Cells and Materials vol. 7, pp. 111-122, 1997.

Gregoire "In Vitro Effects of Calcium-Phosphate Biomaterials on Fibroblastic Cell Behavior" Biology of the Cell vol. 59, pp. 255-260, 1985.

Lindahl et al "Cartilage Repair with Chondrocytes: Clinical and Cellular Aspects" Tissue Engineering of Cartilage and Bone, pp. 175-189, 2003.

Lodish et al "Collagen: The Fibrous Proteins of the Matrix" Molecular Cell Biology, 2000.

Nelson et al "Use of Stem Cells in the Biological Repair of Articular Cartilage" Expert Opinion on Biological Therapy vol. 10, pp. 43-55, 2010.

Oneson et al "The Preparation of Highly Purified Insoluble Collagens" Journal of the American Leather Chemists Association, 1970.

Ringe et al "Stem Cells for Regenerative Medicine: Advances in the Engineering of Tissues and Organs" Naturwissenschaften vol. 89, pp. 338-351, 2002.

Speer et al "A Collagen-Anorganic Bone Composite for Bone Repair: Part 1, In Vivo Study in a Rabbit Radius Defect Model" Transactions of the 31st Annual Meeting of the Society of Biomaterials vol. 29, 2006.

Trafton "New Tissue Scaffold Regrows Cartilage and Bone" Phys.org, 2009.

Wakatani et al "Mesenchymal Cell-Based Repair of Large, Full-Thickness Defects of Articular Cartilage" The Journal of Bone and Surgery vol. 76, pp. 579-592, 1994.

\* cited by examiner

IMPLANTS FOR BONE AND CARTILAGE REPAIR

CROSS-REFERENCE TO RELATED APPLICATIONS

The present application is a continuation of U.S. patent application Ser. No. 15/241,568, filed on Aug. 19, 2016, now U.S. Pat. No. 10,945,846, which is a continuation of U.S. patent application Ser. No. 13/530,297, filed on Jun. 22, 2012 now abandoned. The content of the prior applications is hereby incorporated by reference in its entirety.

BACKGROUND

Articular cartilage covers the ends of all bones that form the articulating joints in humans and animals. In the joint, articular cartilage functions to distribute force, and also serves as a lubricant in the area of contact between the bones. A joint lacking articular cartilage is subjected to stress concentration and friction, thereby preventing ease of motion. Loss of articular cartilage typically leads to painful arthritis and decreased joint motion.

Articular cartilage is an avascular tissue. As a result, when damaged either by trauma or by disease, it does not repair itself. Currently, methods for clinical repair of damaged articular cartilage are limited to the following four modalities: (i) microfracture, (ii) autologous chondrocyte implant (ACI), (iii) mosaicplasty, and (iv) synthetic plug.

Microfracture is a simple arthroscopic procedure and by far the most common method used as a first-line treatment for symptomatic chondral defect. The method, relying on creating microfractures in the subchondral bone, results in diffusion of blood and of bone marrow cells/growth factors into the microfractures, thereby promoting healing.

In the ACI procedure, a small piece of cartilage is harvested from a low weight-bearing area of the knee joint. The chondrocytes in the cartilage fragment are isolated and expanded in culture. After 2 to 3 weeks, the joint is opened and the defect is covered with a periosteal patch obtained from the upper tibial surface. The cell suspension is then injected underneath this patch. The tissue regenerated from this approach is fibrocartilage or hyaline cartilage.

Mosaicplasty involves harvest of multiple cylindrical osteochondral plugs from low-weight-bearing areas within the knee joint and their subsequent transplantation to a chondral defect to create a mosaic pattern. Fibrocartilage tissue grows between the plugs.

Finally, in the synthetic plug technique, a biphasic cylindrical synthetic plug made of synthetic polymers and calcium-containing ceramic particles is inserted into the osteochondral defect of the knee joint. The plug supports the growth of bone and formation of a cartilage layer at the surface of the defect.

None of the above-mentioned techniques are ideal, as patient outcomes are inconsistent from hospital to hospital and from surgeon to surgeon.

The need exists for an improved biocompatible and bioresorbable implant for the repair of bone and cartilage.

SUMMARY

The main objective of this invention is to provide biocompatible and bioresorbable implants for bone and cartilage repair, which eliminate or reduce the disadvantages and problems associated with currently available techniques.

Thus, the main aspect of this invention relates to a biocompatible and bioresorbable implant for the repair of bone and cartilage having a physically and mechanically stable bi-phasic structure. The implant has a cell conductive zone and an osteoconductive zone. Both zones contain a matrix made up of biopolymeric fibers, where the fibers extend from the cell conductive zone into the osteoconductive zone and overlap with the biopolymeric fibers in that zone. The osteoconductive zone includes calcium-containing mineral particles. On the other hand, the cell conductive zone is free of such particles. Additionally, the cell conductive zone and osteoconductive zone are in direct contact with each other.

In another embodiment, a biocompatible and bioresorbable implant for the repair of bone and cartilage includes a single matrix containing biopolymeric fibers. The matrix has a cell conductive zone and an osteoconductive zone. The osteoconductive zone includes calcium-containing mineral particles, while the cell conductive zone is free of calcium-containing mineral particles. The biopolymeric fibers extend from the cell conductive zone into the osteoconductive zone, and the cell conductive zone and the osteoconductive zone are in direct contact with each other.

The details of one or more embodiments of the invention are set forth in the accompanying drawings and the description below. Other features, objects, and advantages of the invention will be apparent from the description and drawing, and from the claims.

DETAILED DESCRIPTION

Figure 1A:
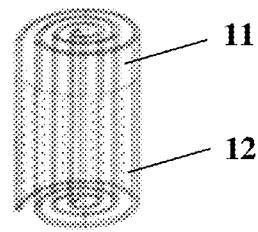
FIG. 1A depicts a cylindrical biocompatible, bioresorbable implant having a cell conductive zone located on top of an osteoconductive zone.

This invention relates to a biocompatible, bioresorbable implant that can be used to repair bone and cartilage.

Thus, the main aspect of this invention is a biocompatible and bioresorbable implant having a physically and mechanically stable bi-phasic structure. The implant includes two separate but mechanically integrated zones, i.e., a cell conductive zone and an osteoconductive zone.

The cell conductive zone contains a matrix formed of biopolymeric fibers. The matrix can be formed of, e.g., elastin, type I, II, or III collagen, as well as natural polysaccharides including animal or human based glycosaminoglycans, shell fish based chitosan, seaweed based alginic acid, and plant based cellulose. Genetically engineered materials can also be used to form the matrix.

Type I and type II collagens are particularly preferred due to their proven biocompatibility and their availability in large quantities. These collagens may be obtained from animal source and from humans using methods well known in the art. For example, the biopolymer fiber matrix can be derived from collagen-rich tissues such as demineralized bone matrix, tendon, and dermis.

The biopolymeric fiber matrix in the cell conductive zone is porous. It can have a pore size of 50 µm to 250 µm such that cells can infiltrate into the internal space of the matrix. As a result, the biopolymeric fiber matrix can be seeded with cells of therapeutic value, e.g., osteoblasts, chondrocytes, stem cells, and bone marrow cells, prior to or during implantation. Such cells of therapeutic value can be isolated using methods well known in the art.

Additionally, growth factors and bioactive substances can be incorporated into the biopolymeric fiber matrix to enhance cartilage regeneration upon implantation. Growth factors that can be incorporated include, but are not limited to EGF, PDGF, bFGF, IGF, and TGF-β. Bioactive substances that can be incorporated include platelet rich plasma, platelet rich fibrin, cell adhesive molecules, cytokines, glycoproteins, proteoglycans, antibiotics, and polysaccharides.

The biopolymeric fiber matrix can have a density of from 0.03 $g/cm^3$ to 0.8 $g/cm^3$, preferably from 0.05 $g/cm^3$ to 0.5 $g/cm^3$. The density can be selected depending on the amount of load expected to be borne by the implant.

The biopolymeric fiber matrix can have a compressive modulus from 0.05 $N/cm^2$ to 10 $N/cm^2$, preferably from 0.1 $N/cm^2$ to 5 $N/cm^2$. This range of compressive modulus provides the mechanical strength required to support the growth of neocartilage during the healing period.

The length of the cell conductive zone can be from 1 mm to 6 mm, preferably from 2 mm to 5 mm, depending on the overall length of the implant.

In one embodiment, the biopolymeric fiber matrix in the cell conductive zone is formed of reconstituted biopolymeric fibers having a length of 1 cm to 50 cm. Preferably, the biopolymeric fibers at the surface of the implant are oriented along the plane of the surface whereas the fibers in the deeper zone, i.e., greater than 2 mm from the surface, are oriented more randomly in space. This fiber arrangement simulates the in vivo structure of the collagen fibers in bone. Alternatively, all of the fibers can be randomly oriented.

In addition to the cell conductive zone described above, the implant also contains an osteoconductive zone. The osteoconductive zone contains a composite matrix formed of biopolymeric fibers and calcium-containing mineral particles. The biopolymeric fibers in the composite matrix can be the same as those described above in the cell conductive zone. The biopolymeric fibers in the cell conductive zone overlap with those in the osteoconductive zone such that the two zones are physically and mechanically integrated. This improves the in vivo stability of the implant and provides it with resistance to shear stress. The composite matrix, similar to the cell conductive matrix, can include various types of cells and bioactive molecules for enhancing bone regeneration. For example, bone morphogenic proteins (BMPs) can be incorporated into the composite matrix.

The calcium-containing mineral particles in the composite matrix can be formed of calcium sulfate or calcium phosphate compounds of various compositions Exemplary calcium phosphate compounds include $Ca_3(PO_4)_2$, $CaHPO_4$ and $Ca_{10}(PO_4)_6(OH)_2$. The particles can also be carbonate apatite $(Ca_{10}(PO_4, CO_3)_6(OH)_2)$ or a mixture of this compound with any of the above-mentioned calcium-containing compounds. Alternatively, calcium-containing silicate based glasses such as 45S5 bioglass can be incorporated into the osteoconductive composite matrix.

The calcium-containing mineral particles in the composite matrix can range in size from 1 µm to as large as 3 mm, preferably from 0.2 mm to 1.5 mm. The ratio of the calcium-containing mineral particles weight to implant weight can be in the range from 95:5 to 30:70, and is preferably from 90:10 to 60:40.

The implant can be in the form of a circular cylinder or an ellipsoidal cylinder. If a circular cylinder, the implant can have a diameter in the range from 0.2 cm to 3.0 cm, preferably from 0.5 cm to 1.5 cm. Its length can be from 0.3 cm to 2.0 cm, preferably from 0.4 cm to 1.5 cm, and more preferably from 0.5 cm to 1.25 cm.

If the implant is in ellipsoidal cylindrical form, its long axis can be from 0.5 cm to 3.0 cm, preferably from 0.5 cm to 1 cm, while its short axis has a dimension smaller than the long axis from 0.4 cm to 1.5 cm, preferably from 0.2 cm to 1 cm.

The implant can be compressed to fit into a delivery device for direct insertion into a defect site. The compressibility can be adjusted by controlling the density of the implant during the manufacturing process. This can be accomplished by adjusting the biopolymer to calcium-particle weight ratio and the degree of hydration of the implant during its formation.

Following insertion, the implant will come into contact with bodily fluids, such as blood, bone marrow, and extracellular fluid. These fluids will hydrate the implant, resulting in its expansion such that it fits tightly in the defect site. In this way, the implant becomes securely anchored.

Figure 1B:
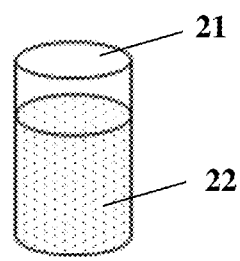
FIG. 1B depicts an alternative embodiment of the cylindrical implant shown in FIG. 1A.
Figure 1C:
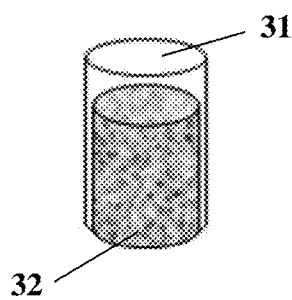
FIG. 1C depicts a cylindrical implant in which a cell conductive zone covers the top and sides of an osteoconductive zone.
Figure 1D:
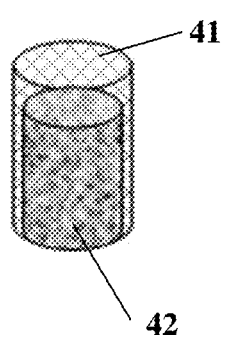
FIG. 1D depicts an alternative embodiment of the implant shown in FIG. 1C.

As shown in FIGS. 1A and 1B, the biocompatible, bioresorbable implant can be in the form of a cylinder in which the cell conductive zone (11, 21) is located on top of the osteoconductive zone (12, 22). Alternatively, as shown in FIGS. 1C and 1D, the cell conductive zone (31, 41) of a cylindrical implant can cover the top and sides of the osteoconductive zone (32, 42), leaving only the bottom surface of it exposed. The two zones can overlap by 0.5 cm and preferably by 1 cm.

In large repair areas, constant friction and shear forces against the implant can dislodge the surface layer. Prior art two-zone devices, such as those described in U.S. Pat. Nos. 7,166,133 and 6,783,712, are characterized by a material and physical distinction between the zones such that one zone can be separated from the other via simple mechanical means. In the current invention, the physical and mechanical integration of the two zones can effectively prevent the cell conductive zone from becoming dislodged by shear stress following implantation in a rotational joint, such as the knee joint. The physical and mechanical unity of the inventive implant's two zone structure is a major improvement over existing two-zone prior art devices.

The implant can be manufactured in a number of different ways. In one preferred embodiment, an aqueous dispersion of biopolymeric fibers is prepared by techniques well known in the art. See U.S. Pat. Nos. 3,157,524 and 5,326,350. The dispersed fibers are homogenized and de-aired to obtain uniformly dispersed fibers prior to a reconstitution step. The short fibers thus produced are reconstituted, i.e., coacervated, by adjusting the pH to the isoelectric point of the fiber, e.g., pH 5 for a purified type I collagen fiber. Alternatively, the reconstitution can be accomplished by adding a neutral salt to the dispersion (e.g., NaCl) to a final salt concentration of about 5% by weight.

The reconstituted fibers are then partially dehydrated via mechanical compression to remove excess amounts of liquid associated with the fibers. The partially dehydrated fibers are then compressed into a sheet of defined size and shape, e.g., a rectangular shape of defined thickness.

Calcium-containing mineral particles are uniformly sprayed over a defined area of the sheet such that the weight percent of the particles to the biopolymeric fibers reaches a predetermined ratio. The sprayed sheet is then rolled up (see FIG. 1A) and placed into a mold having a desired length and diameter. The molded sheet is then freeze-dried in a commercial freeze dryer at a defined temperature and time period that is well known in the art.

The freeze-dried molded sheet is chemically crosslinked to stabilize the matrix. Chemical crosslinking is well known in the art. Common crosslinking agents can be used, including aldehyde compounds, small sugar molecules, carbodiimides, and hexamethylene diisocyanates. The crosslinked matrix is then rinsed to remove any residual crosslinking agent. Alternatively, non-chemical techniques such as dehydrothermal crosslinking and ultraviolet crosslinking can be used. The implant thus produced can then be packaged for sterilization.

In another embodiment, a cylindrical biopolymeric fiber matrix is first fabricated. Reconstituted, partially dehydrated biopolymeric fibers produced as described above are placed into a cylindrical mold and then freeze-dried. The freeze-dried cylindrical matrix is then crosslinked as described above. One end of the crosslinked cylindrical matrix is immersed into an acidic solution of a calcium phosphate compound, e.g., 10% w/v carbonate apatite in 3 M HCl, for a defined period of time, e.g., 10 to 30 minutes, until the solution reaches a level that is approximately 5 mm from the non-immersed end of the cylinder. Calcium and phosphate ions migrate with the solution and fill the interstitial space of the cylindrical matrix. The calcium phosphate ion impregnated matrix is then exposed to an ammonium vapor, such as that generated from 3% $NH_4OH$, to neutralize the acid. At neutral pH, calcium phosphate compounds of several forms will be precipitated out from the solution, forming insoluble calcium phosphate mineral particles within the interstitial space of the matrix. The amount of calcium phosphate mineral particles within the matrix can be controlled by adjusting the concentration of the calcium and phosphate ions in the acid solution. The higher the concentration, the more calcium phosphate mineral particles will be incorporated into the matrix.

In another preferred embodiment, partially dehydrated biopolymeric fibers produced as described above are molded into a cap form having a thickness of approximately 2 mm to 6 mm and a side wall of 1 cm to 2 cm in length having a wall thickness from 0.5 mm to 2 mm. The cap is then freeze dried. The resulting freeze-dried collagen cap can have a density from 0.30 $g/cm^3$ to 0.40 $g/cm^3$. A pre-mixed paste containing biopolymeric fibers and calcium containing mineral particles is then inserted into the cap. The filled cap is then wetted to enhance mechanical integration between the cap and the filling. The filled fiber cap is then placed in a mold and freeze-dried. The final freeze-dried matrix is then crosslinked as described above, thereby forming the implant. In order to increase migration of cells, e.g., osteoblasts, into the matrix implant, the walls of the matrix can be perforated with fine needles.

In yet another embodiment, a cancellous bone block is pre-engineered into a cap form. The bone cap is then thoroughly cleaned by various chemicals to remove adhering materials, such as blood components, cells, and lipids. The bone cap is then subjected to a demineralization step. Commonly used chemicals to remove the mineral component from the bone are inorganic acids such as HCl (0.6 M), or EDTA (0.5 M). The resulting demineralized bone matrix is further subjected to a series of chemical treatments to remove as much as possible non-collagenous materials from the demineralized matrix.

The implant is formed from the demineralized matrix cap as described above for the fiber cap by filling it with a pre-mixed paste containing biopolymeric fibers and calcium containing mineral particles, molding, freeze-drying, and crosslinking.

The implant can be used by creating a bone defect in areas where, as a result of disease, articular cartilage has been depleted and subchondral bone has eroded. The insertion of an implant of the present invention will assist in the repair of both the bone and cartilage structure, thus minimizing pain and improving the range of motion of the joint. The implant is also particularly useful for repairing the sites where osteochondral bone autografts have been harvested to repair an osteochondral defect site, e.g., 1 cm in diameter and 1.5 cm in length.

Without further elaboration, it is believed that one skilled in the art can, based on the description above, utilize the present invention to its fullest extent. The specific examples below are to be construed as merely illustrative, and not limitative of the remainder of the disclosure in any way whatsoever. All references cited herein are hereby incorporated by reference in their entirety.

Example 1

Preparing a Bone and Cartilage Repair Implant

Purified type I collagen fibers (1.25 g) were dispersed in 200 ml of 0.07 M lactic acid (pH 2.3) overnight, homogenized with a Silverson Homogenizer, and then filtered through a 50 mesh stainless steel screen. The resulting acidic dispersion, which had a collagen content of 0.62% (w/v), was placed under vacuum to remove trapped air and stored at 4° C. until use. The purified collagen fibers were prepared essentially as described in U.S. Pat. No. 6,716,225.

Collagen fibers were reconstituted by adding 15 ml of 0.6% $NH_4OH$ to 50 g of the acidic collagen dispersion, thereby adjusting the solution to the isoelectric point of collagen, i.e., pH 4.5-5.0. The reconstituted collagen fibers were partially dehydrated and compressed into a rectangular sheet of about 3 cm×5 cm. Then, 0.72 g of $Ca_{10}(PO_4, CO_3)_6(OH)_2$ mineral particles having a diameter of 0.125 mm to 2 mm was sprayed through a mesh screen over a 3 cm×4.5 cm area of the collagen sheet. The final mineral content of the composite was about 70% by weight of the collagen sheet.

The resulting composite sheet was rolled up to form a spiral implant and then placed into a cylinder shaped mold of 1 cm in diameter and 1.5 cm in length. The cylindrical collagen/mineral composite was freeze dried, followed by crosslinking for 4 hours at ambient temperature using formaldehyde vapor generated from a 0.3% formaldehyde solution. The crosslinked collagen/mineral cylinder was rinsed and then freeze dried, thereby forming a bone and cartilage repair implant.

Example 2

Alternative Preparation Method of a Bone and Cartilage Repair Implant

Approximately 35 ml of 0.6% $NH_4OH$ was added to 200 g of the acidic collagen dispersion described in Example 1 in a 2 L vaccum flask to coacervate the collagen fibers. Excess solution was removed from the fully coacervated fibers by placing them in a perforated mesh basket. The weight of the fibers after this partial dehydration was about 10-20 g. The partilly dehydrated collagen fibers were inserted into a cylindrical mold and lightly compressed using a constant weight for approximately 24 hours. Compression was continued until sufficient water was removed such that the collagen fiber cylinder was 1 cm in diameter and 2 cm in length. The dehydrated collagen fiber plug thus formed was then freeze dried, crosslinked as described in Example 1 above, and rinsed to remove any residual crosslinking agent, thus forming a collagen plug matrix.

One end of the collagen plug matrix was inserted into a 10% w/v solution of carbonate apatite in 3 M HCl for 30 minutes until the solution reached a level that was 5 mm from the top edge of the cylindrical collagen plug matrix. The calcium phosphate ion-impregnated matrix was then removed from the solution and exposed to ammonia vapor to neutralize the acid solution. This neutralization step caused precipitation of the calcium phosphate from the solution, thus forming a collagen plug matrix containing calcium phosphate. The resulting mineral collagen matrix was then freeze dried. By controlling the concentration of the mineral ions in the acid solution, the amount of calcium phosphate minerals content within the matrix can be controlled The amount of mineral incorporated into the matrix was determined by ashing the collagen mineral composite matrix at a temperature of about 550° C. and weighing the mineral. The weight percent of calcium phosphate incorporated into the bone and cartilage repair implant was 52%.

Example 3

Bone and Cartilage Repair Implant Having a Collagen Cap and a Collagen Mineral Composite Approximately 30 g of acidic collagen dispersion prepared as described above in Example 1 was reconstituted by adding 10 ml of 0.6% $NH_4OH$ to the isoelectric point of collagen. The reconstituted collagen fibers were partially dehydrated and placed into a cylindrical-shaped mold of 1 cm in diameter and 2 cm in length. A piston and a washer were used to compress the reconstituted collagen fibers into a cap form having the desired shape and then freeze dried. The resulting freeze-dried collagen cap had a density of 0.35 $g/cm^3$.

Collagen fibers (2.8 g) and 6.5 g of carbonate apatite inorganic bone mineral (particle size <0.35 mm, Collagen Matrix, Inc., Franklin Lakes, New Jersey) were co-dispersed in 200 ml of 0.03 M NaOH (pH 11.5) overnight. The mixture was homogenized with a Silverson homogenizer for 1 minute and de-aired under vacuum. The pH of the mixture was adjusted to between 6.5 and 9 by adding an acidic collagen dispersion prepared as described in Example 1, thereby reconstituting the collagen fibers. The reconstituted collagen mineral composite was de-aired under vacuum and was partially dehydrated over a strainer until a fixed volume was obtained for the final desired density.

The collagen mineral composite was then inserted into the collagen cap. The resulting collagen mineral composite implant was hydrated to enhance interdigitation of collagen fibers in the cap component with the collagen fibers in the mineral composite. The hydrated implant was then molded into a cylindrical dimension, followed by freeze drying. The freeze dried collagen mineral composite was crosslinked and rinsed as described in Example 1 above.

Example 4

Alternative Bone and Cartilage Repair Implant Having a Collagen Cap and a Collagen Mineral Composite A cancellous bone block was pre-shaped into a cap form. The pre-engineered bone cap material was cleaned using multiple steps, among them steam cleansing, detergent washing, water rinsing in a ultrasonic cleaner, sodium hydroxide extracting, and isopropanol extracting to remove adhered tissue, cells, blood components, and lipids. The cleaned bone cap was demineralized by treating it with 0.5 M EDTA for 3 to 6 days The demineralized bone matix (bone collagen cap) was then further purified to remove non-collagenous materials by extraction with sodium hydroxide and hydrochloric acid, rinsing with isopropanol, treating with hydrogen peroxide, and rinsing with water. The resulting purified demineralized bone matrix was then subjected to vacuum-drying.

A collagen mineral composite prepared as described in Example 3 was inserted into the cap-shaped demineralized bone matrix. The implant precursor thus formed was hydrated and molded into a cylindrical dimension to keep its structural shape prior to freeze drying. The resulting freeze dried implant was then crosslinked and rinsed as described in Example 3.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A biocompatible and bioresorbable implant having a physically and mechanically stable bi-phasic structure for the repair of bone and cartilage, comprising a cell conductive zone that contains a first matrix including first biopolymeric fibers, and an osteoconductive zone that contains a second matrix including second biopolymeric fibers and calcium-containing mineral particles, the osteoconductive zone having a top, a bottom, and sides therebetween, wherein the first biopolymeric fibers in the first matrix are derived from tendon or dermis, the cell conductive zone is free of calcium-containing mineral particles, the first biopolymeric fibers extend into the osteoconductive zone and overlap with the second biopolymeric fibers such that the cell conductive zone and the osteoconductive zone are physically and mechanically integrated, the cell conductive zone overlaps with and is in direct contact with the osteoconductive zone, the cell conductive zone covering the top and sides of the osteoconductive zone leaving the bottom of the osteoconductive zone exposed, the first biopolymeric fibers and the second biopolymeric fibers at a surface of the implant are oriented along a plane of the surface, and the first biopolymeric fibers and the second biopolymeric fibers located greater than 2 mm from the surface are randomly oriented.

2. The implant of claim 1, wherein the first biopolymeric fibers include a protein.

3. The implant of claim 2, wherein the protein is a fibrillar collagen.

4. The implant of claim 3, wherein the collagen is type I collagen, type II collagen, or type III collagen.

5. The implant of claim 1, wherein the calcium-containing mineral particles include synthetic or natural calcium-containing compounds.

6. The implant of claim 1, wherein the first matrix has a density of 0.03 g/cm$^3$ to 0.8 g/cm$^3$ and a compressive modulus of 0.05 N/cm$^2$ to 10 N/cm$^2$.

7. The implant of claim 6, wherein the shape of the implant is a circular cylinder.

8. The implant of claim 7, wherein the implant has a length of 0.3 cm to 2 cm and a diameter of 0.2 cm to 3 cm.

9. The implant of claim 8, wherein a content of mineral particles is from 30% to 95% by weight of the implant.

10. The implant of claim 9, wherein a length of the cell conductive zone is 10% to 60% of the length of the implant.

11. The implant of claim 10, wherein the implant length is 0.5 cm to 1.25 cm, the diameter is 0.5 cm to 1.5 cm, the content of mineral particles is from 60% to 90% by weight of the implant, the length of the cell conductive zone is 15% to 40% of the length of the implant, the calcium-containing compounds are carbonate-containing apatite, and the first matrix has a density of 0.05 g/cm$^3$ to 0.5 g/cm$^3$ and a compressive modulus of 0.1 N/cm$^2$ to 5.0 N/cm$^2$.

12. The implant of claim 1, further comprising a bioactive molecule.

13. The implant of claim 12, wherein the bioactive molecule is a growth factor, a cell adhesive molecule, a cytokine, a glycoprotein, a proteoglycan, an antibiotic, or a polysaccharide.

14. The implant of claim 1, further comprising cells.

15. The implant of claim 14, wherein the cells are osteoblasts, chondrocytes, stem cells, or bone marrow cells.

16. A biocompatible and bioresorbable implant for the repair of bone and cartilage, comprising a matrix that contains biopolymeric fibers, the matrix having a cell conductive zone and an osteoconductive zone, wherein the osteoconductive zone includes calcium-containing mineral particles, the osteoconductive zone having a top, a bottom, and sides therebetween, the cell conductive zone is free of calcium-containing mineral particles, the biopolymeric fibers extend from the cell conductive zone into the osteoconductive zone, the biopolymeric fibers are derived from tendon or dermis, the cell conductive zone is in direct contact with the osteoconductive zone, the cell conductive zone covering the top and sides of the osteoconductive zone leaving the bottom of the osteoconductive zone exposed, the biopolymeric fibers at a surface of the implant are oriented along a plane of the surface, and the biopolymeric fibers located greater than 2 mm from the surface are randomly oriented.

17. The implant of claim 16, wherein the biopolymeric fibers include a fibrillar collagen and the calcium-containing mineral particles are present at 60% to 90% by weight of the implant.

18. The implant of claim 17, wherein the fibrillar collagen is type I collagen and the calcium-containing mineral particles are carbonate apatite particles.

19. The implant of claim 18, wherein the implant is cylindrical, having a length of 0.5 cm to 1.25 cm and a diameter of 0.5 cm to 1.5 cm, and the cell conductive zone has a length equal to 15% to 40% of the implant length.

20. The implant of claim 19, wherein the cell conductive zone has a density of 0.05 g/cm$^3$ to 0.5 g/cm$^3$ and a compressive modulus of 0.1 N/cm$^2$ to 5 N/cm$^2$.

* * * * *